(12) United States Patent
Maples et al.

(10) Patent No.: US 12,144,340 B2
(45) Date of Patent: Nov. 19, 2024

(54) DEVICES, SYSTEMS, AND METHODS FOR PACKAGING AND TRANSPORT OF BIOLOGICAL TISSUE

(71) Applicant: Abeona Therapeutics Inc., New York, NY (US)

(72) Inventors: Phillip B. Maples, Concord Township, OH (US); Clarisse Rogat, Shaker Heights, OH (US); William G. Teags, Longmont, CO (US)

(73) Assignee: Abeona Therapeutics Inc., Cleveland, OH (US)

( * ) Notice: Subject to any disclaimer, the term of this patent is extended or adjusted under 35 U.S.C. 154(b) by 0 days.

(21) Appl. No.: 17/626,987

(22) PCT Filed: Jul. 16, 2020

(86) PCT No.: PCT/US2020/042411
§ 371 (c)(1),
(2) Date: Jan. 13, 2022

(87) PCT Pub. No.: WO2021/011821
PCT Pub. Date: Jan. 21, 2021

(65) Prior Publication Data
US 2022/0295783 A1    Sep. 22, 2022

Related U.S. Application Data

(60) Provisional application No. 62/874,666, filed on Jul. 16, 2019.

(51) Int. Cl.
*A01N 1/02* (2006.01)
*A61F 2/00* (2006.01)
(Continued)

(52) U.S. Cl.
CPC .......... *A01N 1/0273* (2013.01); *A61F 2/0095* (2013.01); *B65B 5/04* (2013.01);
(Continued)

(58) Field of Classification Search
CPC ....... A01N 1/0273; A61F 2/0095; B65D 5/04; B65D 55/04
See application file for complete search history.

(56) References Cited

U.S. PATENT DOCUMENTS 5,090,568 A * 2/1992 Tse .......................... G02B 21/34
                                                        220/4.23
5,090,571 A * 2/1992 Walker .................. A61B 50/30
                                                        220/23.9
(Continued)

FOREIGN PATENT DOCUMENTS

WO    WO-2021/011821    1/2021

OTHER PUBLICATIONS

PCT/US2020/042411, International Search Report and Written Opinion mailed Oct. 29, 2020, 16 pages.
(Continued)

*Primary Examiner* — Anthony D Stashick
*Assistant Examiner* — Blaine G Neway
(74) *Attorney, Agent, or Firm* — COOLEY LLP

(57) ABSTRACT

Embodiments of the present disclosure are directed to a biological tissue packaging system, as well as a transport system, and, in some embodiments, comprises a first package, a secondary package, and a tertiary package. Each of the first, second, and tertiary packages is sterilized prior to packaging of a biological tissue therein. The first package comprises a pouch, and a first tray and a first lid configured for removable snap-fit attachment to one another so as to form a clamshell container. The secondary package is configured to contain the first package and interlock therewith.
(Continued)

The tertiary package is configured to contain the secondary package and interlock therewith.

3 Claims, 6 Drawing Sheets

(51) Int. Cl.
| | |
|---|---|
| *B65B 5/04* | (2006.01) |
| *B65B 7/28* | (2006.01) |
| *B65B 55/04* | (2006.01) |
| *B65D 21/02* | (2006.01) |
| *B65D 43/16* | (2006.01) |
| *B65D 77/04* | (2006.01) |
| *B65D 79/02* | (2006.01) |
| *B65D 81/127* | (2006.01) |
| *B65D 81/22* | (2006.01) |

(52) U.S. Cl.
CPC ............ *B65B 7/2878* (2013.01); *B65B 55/04* (2013.01); *B65D 21/0212* (2013.01); *B65D 43/162* (2013.01); *B65D 77/0406* (2013.01); *B65D 77/0433* (2013.01); *B65D 77/046* (2013.01); *B65D 79/02* (2013.01); *B65D 81/127* (2013.01); *B65D 81/22* (2013.01); *B65D 2543/00194* (2013.01); *B65D 2543/00296* (2013.01); *B65D 2543/00509* (2013.01); *B65D 2543/00537* (2013.01); *B65D 2543/00555* (2013.01); *B65D 2543/00657* (2013.01); *B65D 2543/00685* (2013.01); *B65D 2543/00759* (2013.01); *B65D 2543/00796* (2013.01); *B65D 2543/00842* (2013.01)

(56) References Cited

U.S. PATENT DOCUMENTS

| | | | |
|---|---|---|---|
| 5,236,088 | A | 8/1993 | Dhority et al. |
| 5,415,282 | A | 5/1995 | Kienholz |
| 6,449,959 | B1 | 9/2002 | Garcia |
| 6,889,839 | B1 | 5/2005 | Rosten et al. |
| 9,598,218 | B2 | 3/2017 | Hallab |
| 9,604,026 | B2 * | 3/2017 | Gribb .................. A61M 16/109 |
| 10,537,098 | B2 * | 1/2020 | Matsumura .......... A01N 1/0268 |
| 10,695,157 | B2 * | 6/2020 | Poyss ...................... B65B 25/00 |
| 2014/0202908 | A1 | 7/2014 | Liburd et al. |
| 2016/0008120 | A1 | 1/2016 | Benoit et al. |
| 2018/0007890 | A1 | 1/2018 | Matsumura |
| 2018/0193127 | A1 | 7/2018 | Poyss et al. |

OTHER PUBLICATIONS

PCT/US2020/042411, International Preliminary Report on Patentability mailed Jan. 18, 2022, 13 pages.

* cited by examiner

DEVICES, SYSTEMS, AND METHODS FOR PACKAGING AND TRANSPORT OF BIOLOGICAL TISSUE

CROSS-REFERENCE TO RELATED APPLICATIONS

This application is a national stage application, filed under 35 U.S.C. 371, of International Application No. PCT/US2020/042411, filed on Jul. 16, 2020, which claims priority to, and the benefit of U.S. Provisional Patent Application No. 62/874,666, filed on Jul. 16, 2019. The contents of each of the aforementioned patent applications are incorporated herein by reference in their entireties.

BACKGROUND

In autologous cell therapies, a patient's own cells are biopsied, and then cultured, expanded and treated outside the body before being reintroduced into the donor. In some cases, the patient's cells must be transported to a treatment location distant from where the patient's biopsy was taken, and then transported back to the patient's location in order to be reintroduced into the patient. Accordingly, the cells must remain alive, intact, and undamaged during transport and must be transported under conditions designed to minimize post-treatment physical and biological degradation before administration to the patient. The cells thus require very careful handling and an appropriate protective packaging and transport system.

Developing such an appropriate transport system poses many problems, including configuring a case/package that adequately fits the biological product (in some cases, perfectly), while taking into consideration features including, for example, the presence of clips at the edge, and one or more sutures (depending upon the tissue product). Thus, the packaging must:

minimize tensions (in the tissue product),
allow constant fluid feeding of the tissue product, but limit fluid movement (to avoid a "rubbing effect"),
keep the tissue product from floating/deforming/curling in the culture medium,
avoid the formation/presence of bubbles,
be constructed from non-toxic materials,
be practical for operators to use, and
be cable of sterilization.

SUMMARY OF SOME OF THE EMBODIMENTS

In some embodiments of the present disclosure, a biological tissue packaging and transport system is provided and comprises a first package, a secondary package, and a tertiary package. Each of the first, second, and tertiary packages is sterilized prior to packaging of a biological tissue therein. The first package comprises a pouch, and a first tray and a first lid configured for removable snap-fit attachment to one another so as to form a clamshell container. The secondary package is configured to contain the first package and interlock therewith. The tertiary package is configured to contain the secondary package and interlock therewith.

In some such embodiments, one or more of the following additional structures, functionality, steps, and/or clarifications (and in some embodiments, a plurality of the following, and in some embodiments, a majority of the following, and in yet some further embodiments, all of the following) is included, yielding yet further embodiments of the disclosure:

the clamshell container is configured to house at least one biological tissue and liquid transport media, and/or minimize movement of the transport media;

the tray of the clamshell can include at least one tray channel and at least one tray projecting portion arranged along the perimeter of the tray, and optionally also a raised portion, relative to the at least one tray channel, arranged within the perimeter of the tray;

the raised portion can be configured for at least one of: arrangement of the biological tissue thereon, to accept placement of the biological tissue and a clipped and/or sutured perimeter of the biological tissue to extend over and/or into the at least one tray channel; and to include a knurled surface, a recessed area arranged substantially in the center of the raised portion so as to provide relief for an identifying suture;

the lid can include at least one of a finger-lift tab, a plurality of protrusions configured to hold clips along the perimeter, and at least one lid channel and at least one lid projecting portion arranged along a perimeter of the lid and configured to mate with at least one of the tray channel and the tray projecting portion;

the at least one channel of either or both of the tray and lid channel may be configured to enable transport media to circulate within the first/clamshell package/container;

the lid projecting portion (see above) can include a surface configured to at least one of contact and hold a perimeter of a biological tissue arranged on the raised portion of the tray;

the lid can include a pair of holes, which each can be located in a respective, opposed corner of the lid and configured so as to expedite the removal of trapped air within the clamshell container during a liquid media filing process;

the lid can include a plurality of dimples configured to project out from an inner surface of the lid, where the plurality of dimples can be configured to at least one of establish a tortuous path for the transport media upon flowing over the biological tissue, reduce the velocity of the flow of the transport media, limit contact area of the lid on the biological tissue, and limit potential damage to the biological tissue due to movement of the biological tissue towards and contact with the lid;

the pouch can include at least one of a sealable portion configured to receive the clamshell container, at least one first sealable port configured to receive the liquid transport media, at least one second sealable port configured to evacuate air from at least an interior of the pouch, and at least one substantially transparent portion for viewing at least a portion of the clamshell container arranged within the pouch (such transparent portion can allow the viewing of air/bubbles/other within);

the pouch can also include a visualization label (re: information on the product contained therein);

the secondary package can comprise a second tray and a second lid, where the second tray and second lid are configured for removable attachment to one another so as to form a second container, and can also include at least one secondary barrier film removably sealed to at least one of an exterior side of the second tray and
second lid (e.g., to enable containment of fluid/media
upon opening);
at least a portion of the second container can be at least
one of: configured to be substantially transparent so as
to view at least a portion of the first package contained
therein, and configured to be substantially gas imper-
meable (can be a separate portion from the transparent
portion);
the second container can also include a visualization label
(re: information on the product contained therein);
the tertiary package can comprise a third tray and a third
lid, where the third tray and third lid can be configured
for removable attachment to one another so as to form
a tertiary container, and can also include at least one
tertiary barrier film removably sealed to at least one of
an exterior side of the third tray and third lid;
the tertiary container can also include a visualization label
(re: information on the product contained therein);
the tertiary container structure, in some embodiments,
enables the minimization of temperature variations
and/or light exposure of the contents;
at least a portion of the third container can be substantially
transparent so as to view at least a portion of the first
package contained within the second container;
a transport container, which can comprise a box, a shock
absorbing insert element, an adaptor element, a shock
absorbing lid, and an environmental sensor;
the box can be configured to contain the insert element,
the adaptor, and the lid,
at least one of the adaptor and insert element can be
configured to hold the tertiary container substantially
in place relative to the box, and
the environmental sensor can be configured for moni-
toring at least one environmental parameter of the
interior of the box; and
each of the first, secondary, and tertiary package can be
sterilized (preferably) prior to packaging of a biological
tissue.
In some embodiments, a biological tissue packaging and
transport method is provided and comprises at least a
plurality of the following steps (in some embodiments, all of
the following steps): warming a liquid transport medium for
a biological tissue for packing to a predetermined tempera-
ture, sterilizing components of a biological packaging sys-
tem, placing a biological tissue for transport on a base/raised
platform of a first tray of a clamshell container, adding a
predetermined amount of transport media to the first tray, the
media configured to keep the biological tissue moist, secur-
ing a first lid of the clamshell container to the first tray,
placing the clamshell container containing the biological
tissue into a pouch via an opening, sealing the opening end
of the pouch, substantially filling the pouch with transport
media via one and/or another of a plurality of ports of the
pouch, such that, one of the ports performs as liquid trans-
port, and another as a vent, placing the pouch with the
clamshell container therein into a secondary package, seal-
ing the secondary package, optionally via a barrier film,
placing the secondary package within a tertiary package,
sealing the tertiary package, optionally via a barrier film, and
placing the tertiary package within a shipping container/box.
In some such embodiments, one or more of the following
additional structures, functionality, steps, and/or clarifica-
tions (and in some embodiments, a plurality of the follow-
ing, and in some embodiments, a majority of the following,
and in yet some further embodiments, all of the following)
is included, yielding yet further embodiments of the disclo-
sure:
providing a biological tissue packaging and transport
system comprising at least one of the clamshell con-
tainer, the pouch, the secondary package, the tertiary
package, and the shipping container/box;
providing a biological tissue packaging and transport
system comprising at least two of the clamshell con-
tainer, the pouch, the secondary package, the tertiary
package, and the shipping container/box;
providing a biological tissue packaging and transport
system comprising the clamshell container, the pouch,
the secondary package, the tertiary package, and the
shipping container/box;
providing a biological tissue packaging and transport
system comprising at least one of the clamshell con-
tainer, the pouch, the secondary package, the tertiary
package, and the shipping container/box;
providing a biological tissue packaging and transport
system according to any one or more of the packaging
and transport systems disclosed herein;
packaging occurs within a laminar flow hood;
the liquid transport media is warmed to approximately 37
degrees C.;
the liquid transport media is warmed via a water bath; and
sealing is performed via at least one of heat sealing, an
adhesive, and a barrier film.
Further details of at least some of the above-noted
embodiments, as well as other embodiments, including
objects and advantages thereof, can be found in the detailed
description which follows, as well as in the figures included
with this disclosure, a brief description of which is provided
below.

DETAILED DESCRIPTION OF SOME OF THE EMBODIMENTS

Figure 1A:
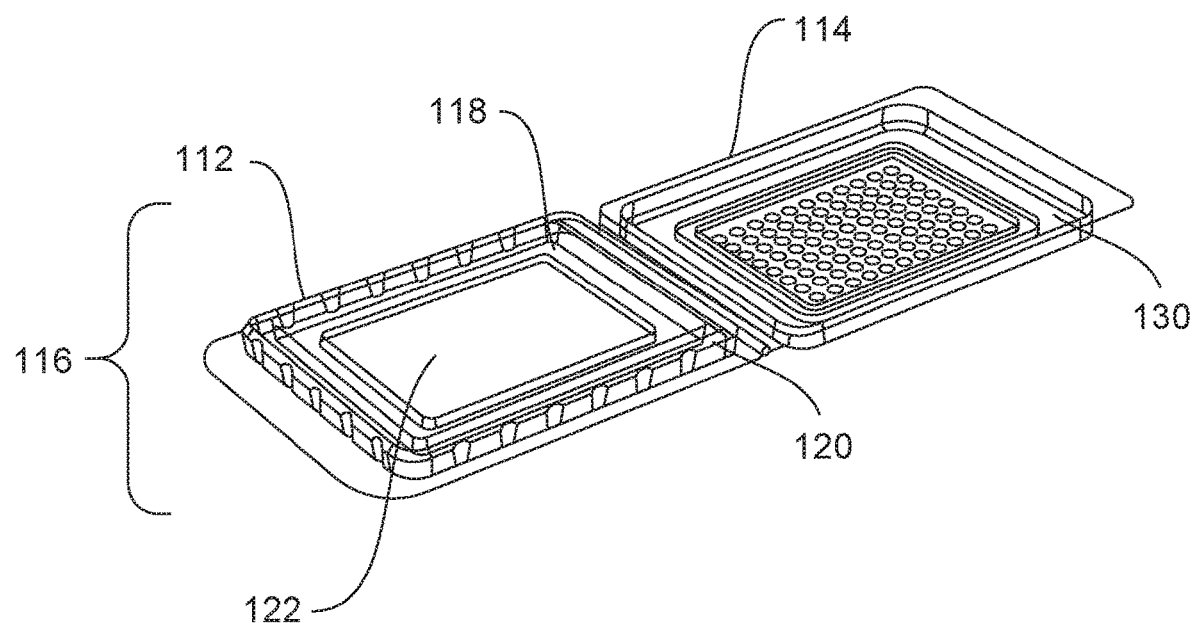
FIG. 1A is a perspective view of a clamshell component
of a first package for a biological packaging system ("BPS")
according to some embodiments of the disclosure.
Figure 1B:
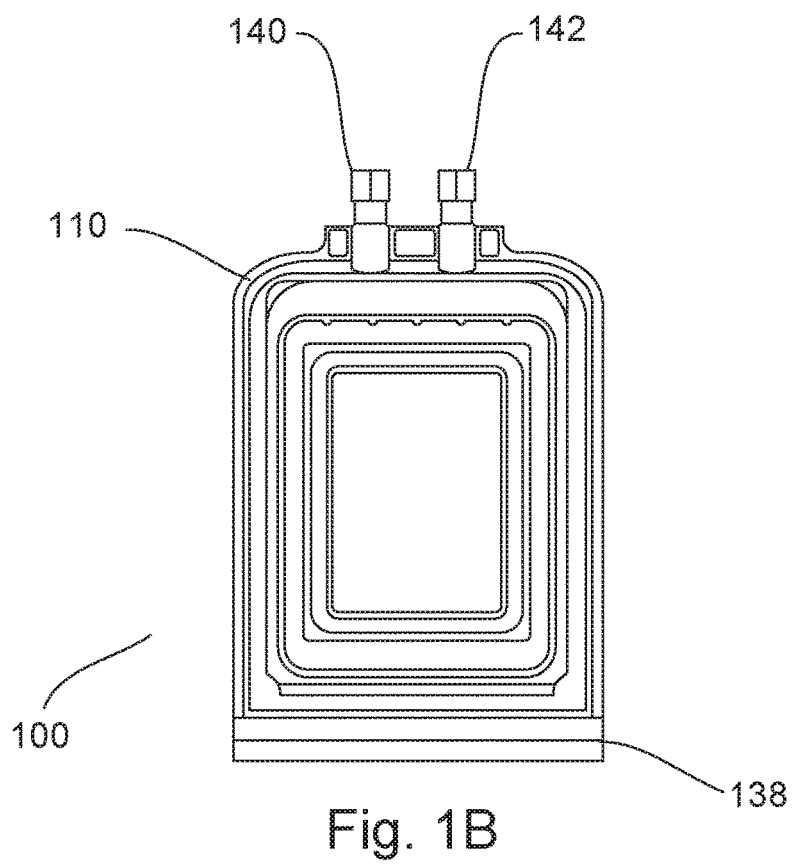
FIG. 1B is a front view of the first package of the BPS
according to some embodiments of the disclosure.

FIGS. 1A-5 illustrate various embodiments of the present disclosure for a biological tissue packaging (BPS) and transport system, including a series of aseptic containers so as to establish a monitored, safe and gentle environment during transportation of a biological component/tissue. According to some embodiments, such a system can include a first package (see FIGS. 1A-1B, 2A-2D), a secondary package (see FIGS. 3A-3B), and a tertiary package (see FIGS. 4A-4B). In some embodiments, the system can also include a transport container (see FIG. 5) for containing the first, secondary, and tertiary packages. One of skill in the art will understand and appreciate that manufacture of the various containers/packages and components, according to some embodiments, is made from a clear plastic material (e.g., evidenced by the line drawings of FIGS. 1A-4B).

One of skill in the art will appreciate that the components of the packaging system, including any of the first, secondary, and tertiary packages, may be manufactured according to standard and well known manufacturing processes (e.g., thermoforming, injection and blow molding, stamping, additive, extrusion, rotational, compression, casting), and in some embodiments, clear plastic, which in some embodiments, aids in viewing material within each package.

Accordingly, in some embodiments, one or more, and preferably each of the first, secondary, and tertiary packages is sterilized prior to packaging of a biological tissue therein by any means known in the art (e.g., gaseous/vapor materials, UV), preferably performed under a laminar flow hood (for example). Of course, any of the components of at least some of the embodiments may be pre-sterilized prior to assembly with other components.

As shown in FIGS. 1A-2B, the first or primary package 100, in some embodiments, comprises a pouch 110 (which can be similar to a Fenwal 600ml Transfer Pack with openings therein), and a tray 112 and a lid 114 configured for removable snap-fit attachment to one another so as to form a clamshell container 116 (any of the foregoing can be configured to include a pin, spike-port, and/or cannula). The clamshell container 116 is configured to, at least one of house at least one biological tissue and (preferably, but optionally) liquid transport media, and accordingly, minimize movement of the transport media. As shown in FIG. 2A, the tray 112 includes at least one tray channel 118 and at least one tray projecting portion 120 arranged along the perimeter of the tray, and a raised portion 122, relative to the at least one tray channel 118, arranged within the perimeter of the tray. In some embodiments, a flap portion 119, which may be arranged along the perimeter of the raised portion 122, so as to interact with a corresponding projecting portion of the lid 114. In some embodiments, such a flap portion, may be integral with the material of the tray, and in some embodiments, can be configured to interact with the lid for additional sealing purposes; accordingly, in some embodiments, flap 119 is flexible so as to be able to conform to one and/or another respective feature of the tray (see, e.g., FIG. 2A, the left-most flap being bent/flexed). Alternatively, and as illustrated in FIG. 2A, flap portion 119 represents a perimeter of a separate item placed on raised portion 122.

Specifically, in some embodiments, flap portion 119 represents a separate component, including, for example, in some embodiments, represents and corresponds to the perimeter of a biological tissue material placed on raised portion 122 (for containment/shipment by embodiments of the disclosure). To that end, the perimeter of the biological tissue represents flap 119 that interacts with at least one perimeter portion of the lid 114 (as well as, in some embodiments, at least one perimeter portion of the tray 112), e.g., lid projecting portion 132, and/or tray channel 118. Accordingly, for embodiments representing a biological tissue to be packaged and transported, flap 119 in FIG. 2A would represent a separate item, and thus, a solid line between item no. 122 and 119 as illustrated. This perimeter portion of the tissue, upon interacting with at least one of (and preferably both) the perimeter portions (e.g., projecting portion(s), channel portion(s)), enable at least one (and preferably both of—in some embodiments), the holding of the biological tissue, and sealing thereof within the clamshell container.

The raised portion 122, in some embodiments, can be configured for arrangement of a biological tissue thereon, to accept placement of the biological tissue and a clipped and/or sutured perimeter of the biological tissue to extend over and/or into the at least one tray channel 118 (e.g., see flap 119 described above, according to some embodiments), and includes, in some embodiments, a knurled or corrugated surface (FIG. 2A), and a recessed area 126 (FIG. 2D) arranged substantially in the center of the raised portion so as to provide relief for an identifying suture (for example). In some embodiments, the tissue is centered on the raised portion such that hemoclip sutures arranged along a perimeter of the tissue are arranged over the channel 118. After alignment, placement and inspection, a few drops of media can be added to the tissue to assure it remains moist during assembly procedures. The tray may be filled with media before placement of a product so as to evacuate as much air as possible. In some embodiments, the pouch may be made from plasticized PVC (DEHP), ethylene vinyl acetate (EVA), fluorinated ethylene polypropylene (FEP), and the like.

Figure 2A:
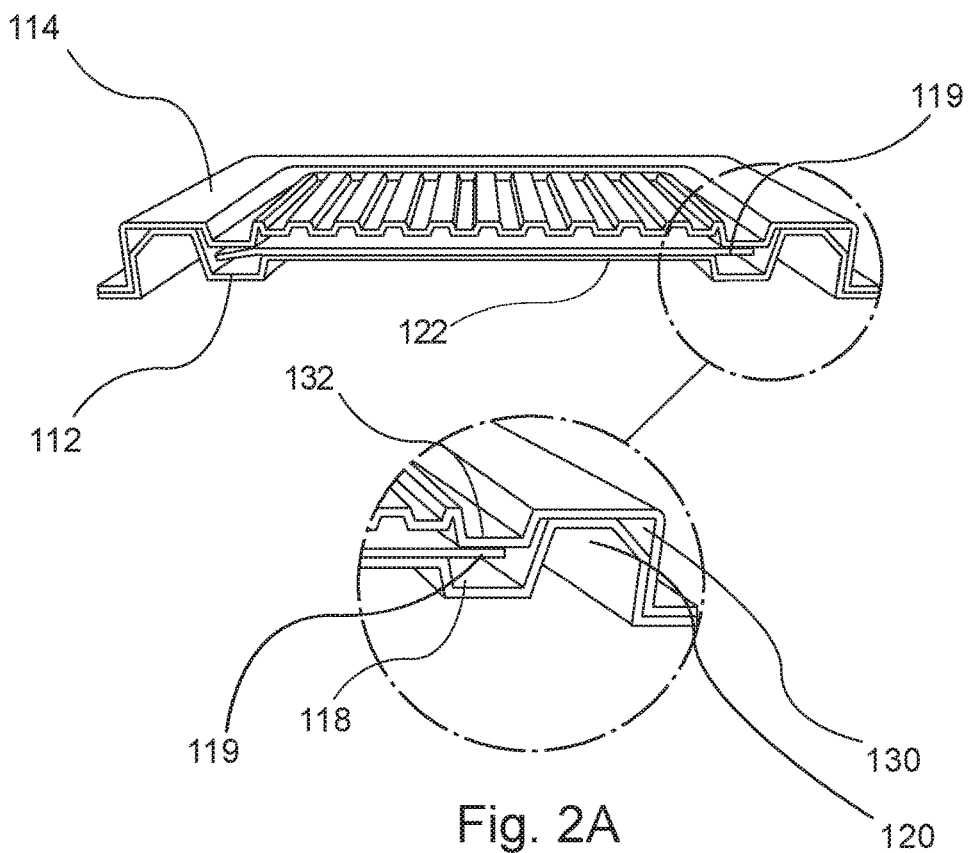
FIG. 2A is a cross-section of the clamshell component of
the first package for the BPS according to some embodi-
ments of the disclosure, and includes an enlargement of the
edge/perimeter interlocking functionality.
Figure 2B:
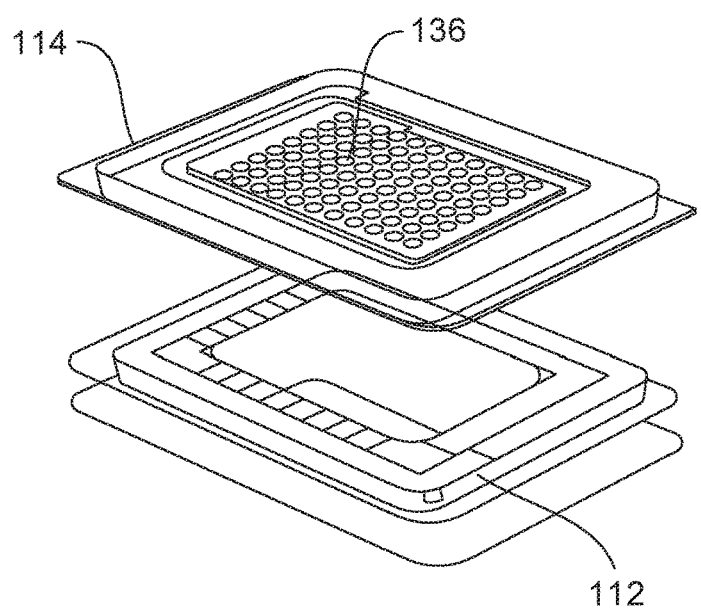
FIG. 2B is a perspective, exploded view of the clamshell
package holding a biological tissue on a raised portion of the
bottom tray thereof, for a BPS according to some embodi-
ments of the disclosure.
Figure 2C:
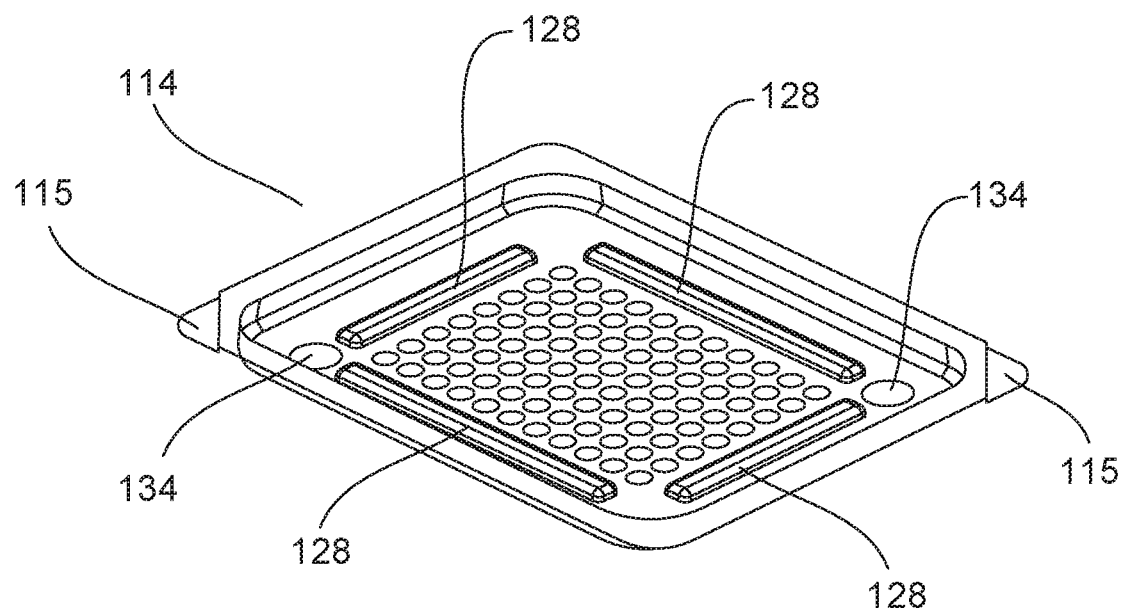
FIG. 2C is a perspective view of a lid component for a
clamshell component for the first package of the BPS,
according to some embodiments of the disclosure.
Figure 2D:
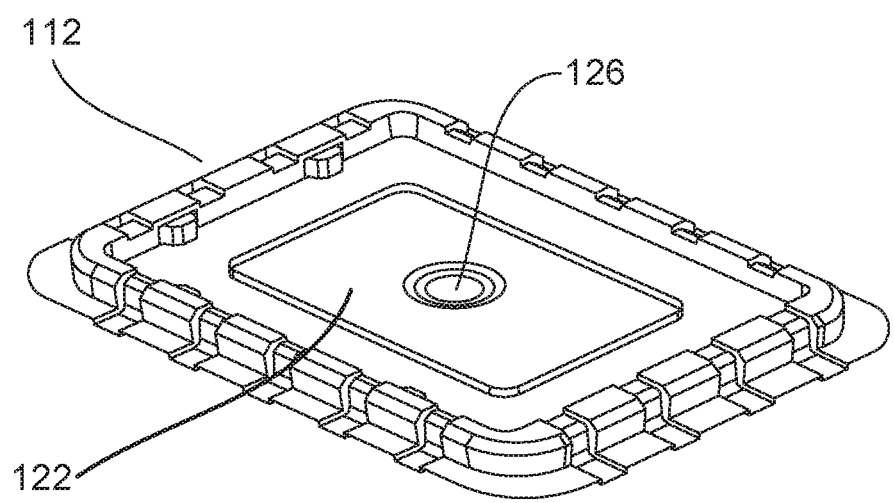
FIG. 2D is a perspective view of a tray component for a
clamshell component for the first package of the BPS,
according to some embodiments of the disclosure.
Figure 3A:
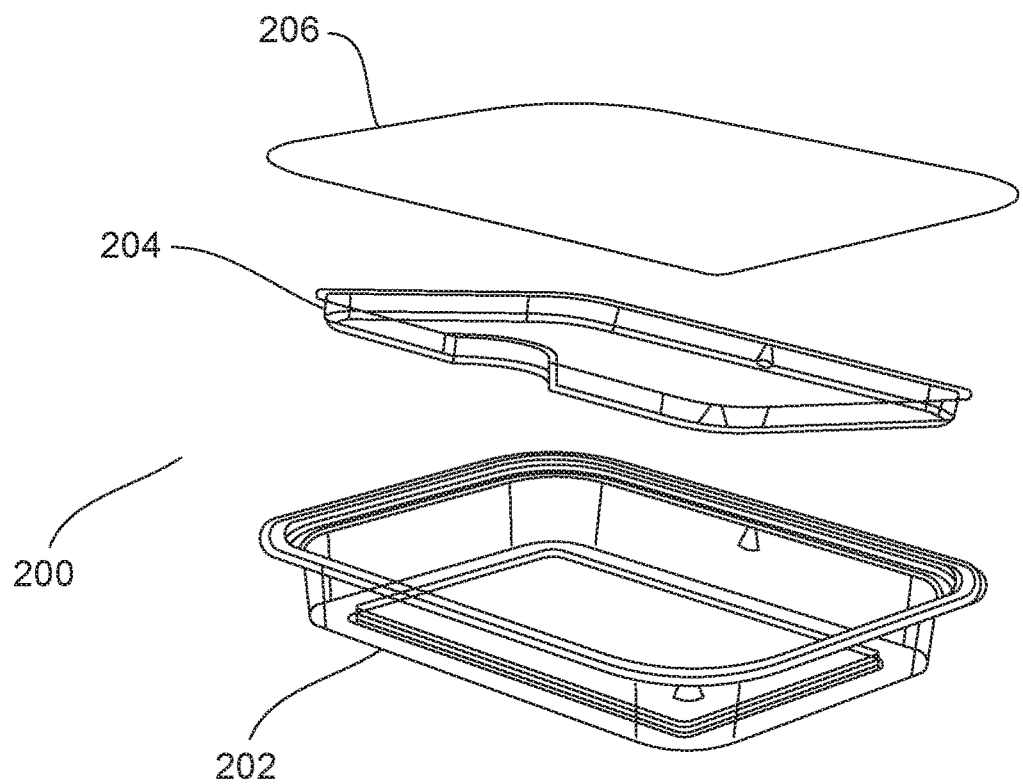
FIG. 3A is a perspective, exploded view of a secondary
package for a BPS, according to some embodiments of the
disclosure.
Figure 3B:
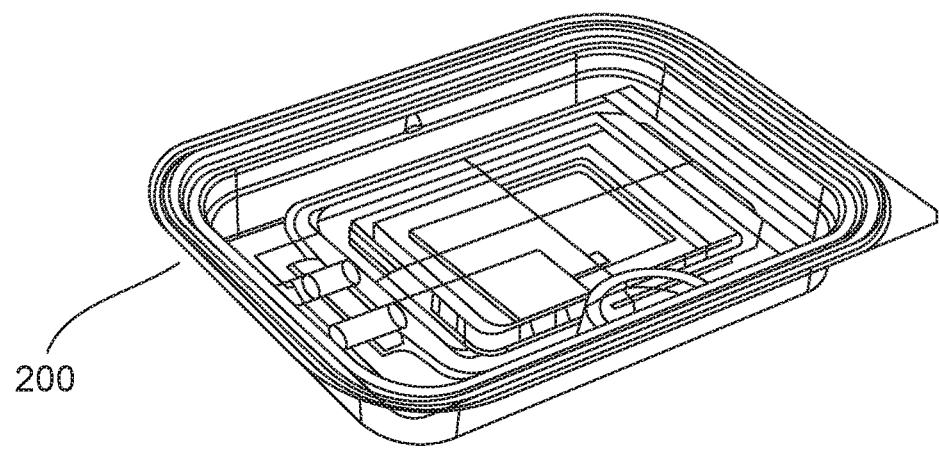
FIG. 3B is a perspective view of an assembled secondary
package for the BPS, configured to hold a first package of
the according to some embodiments of the disclosure.

In some embodiments, the lid 114 includes at least one of a finger-lift tab 115 (FIG. 2C), one or more, and preferably, a plurality of protrusions 128, which may also be referred to as locating bars, at or near/proximate the perimeter of the lid 114, which may be configured to interact with and/or hold clips that may be arranged along a perimeter of the biological tissue placed within the clamshell container (and within the center of the container). Lid 114, as shown in FIG. 2A (which illustrates some embodiments of lid 114 having a corrugated/knurled center portion as opposed to the dimpled center portion, according to some embodiments, of FIG. 1A, 2B and 2C), can include at least one lid channel 130 and at least one lid projecting portion 132 arranged along a perimeter of the lid. Such channel(s)/projecting portion(s) can be configured to mate with, for example, at least one tray channel (e.g., 118 of FIG. 1A, and/or tray projecting portion 120, FIG. 1A), where the lid projecting portion 132 includes a surface configured to at least one of contact and hold a perimeter of a biological tissue arranged on the raised portion of the tray, and in some embodiments, such functionality including interaction with flap 119 (as noted above, in some embodiments, flap 119 corresponds to the perimeter of biological tissue positioned on the center raised portion of the tray 112).

The lid 114, according to some embodiments, can also include one or more, and in some embodiments preferably a pair, of holes 134, each located in a respective, opposed corner of the lid, each of which can be configured to expedite the removal of trapped air within the clamshell container during a liquid media filing process (for example). In some embodiments, a plurality of dimples 136, can be included with the lid, which can project out from an inner surface of the lid and can be configured to at least one of establish a tortuous path for the transport media upon flowing over the biological tissue, reduce the velocity of the flow/circulation of the transport media, and limit contact area of the lid on the biological tissue. One and/or another of such features/functionality can limit potential damage to the biological tissue due to movement of the biological tissue towards and contact with the lid.

The pouch 110, of the first package, according to some embodiments, includes a sealable portion 138, which can be one or more sides of the pouch, where at least one of which is configured to receive the clamshell container 116, at least one first sealable port 140 configured to receive the liquid transport media, and at least one second sealable port 142 configured to evacuate air from at least an interior of the pouch (or vice-versa re: port 140). Each port can be fitted with a luer lock connection. The pouch may also include at least one substantially transparent portion for viewing at least a portion of the clamshell container 116 arranged within the pouch.

The BPS, in some embodiments, includes a/the secondary package 200 is configured to contain the first package 100 and interlock therewith (preferably), and, in some embodiments, the second package 200 includes a tray 202 and a lid 204, the tray and lid configured for removable attachment to one another so as to form a container. The secondary package may further include at least one barrier film 206, which can be removably sealed to at least one of an exterior side of the tray and lid. In some embodiments, at least a portion of the second container 200 is substantially transparent so as to view at least a portion of the first package contained therein, and, in some embodiments, the second container is configured to be substantially gas impermeable. Interlocking may be accomplished via a shaped design, such that one component/package, for example, includes a projecting portion which is received by a recess or opening in the second component/package.

Figure 4A:
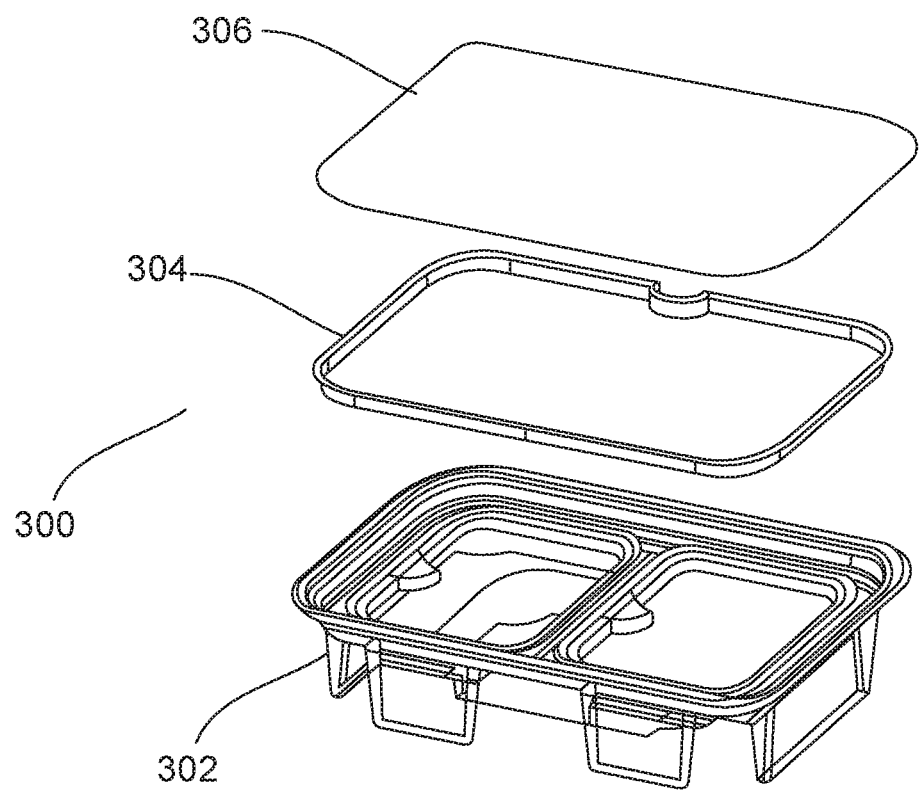
FIG. 4A is a perspective, exploded view of a tertiary
package for a BPS, according to some embodiments of the
disclosure, which can be configured to hold, in some
embodiments, a plurality of second packages (according to
some embodiments)
Figure 4B:
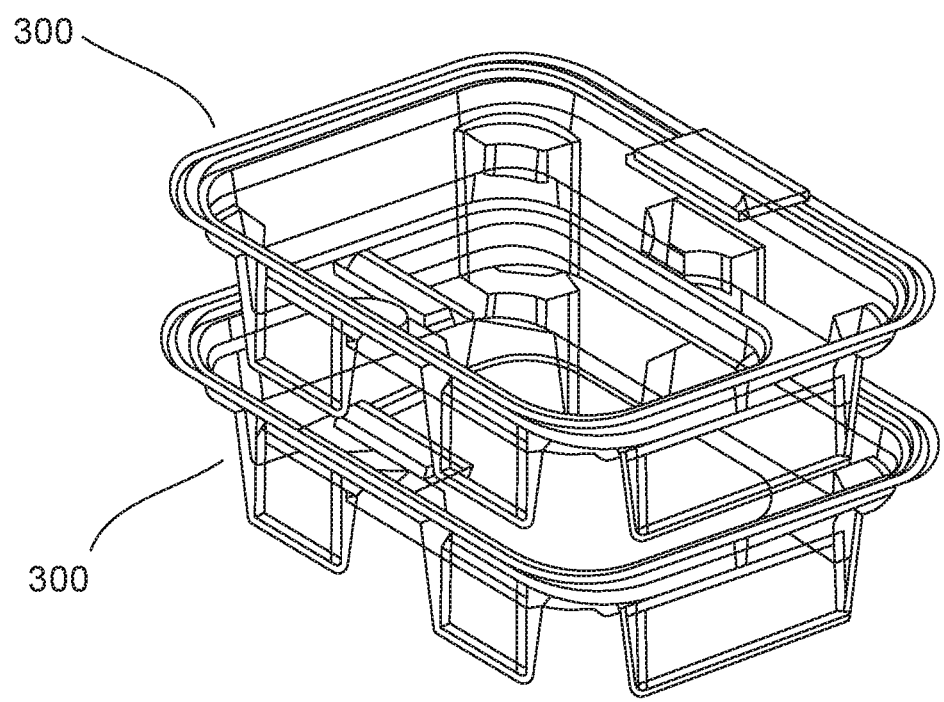
FIG. 4B is a perspective view of an assembled tertiary package for a BPS, according to some embodiments of the disclosure, illustrating, according to some embodiments, two-stacked tertiary packages.
Figure 5:
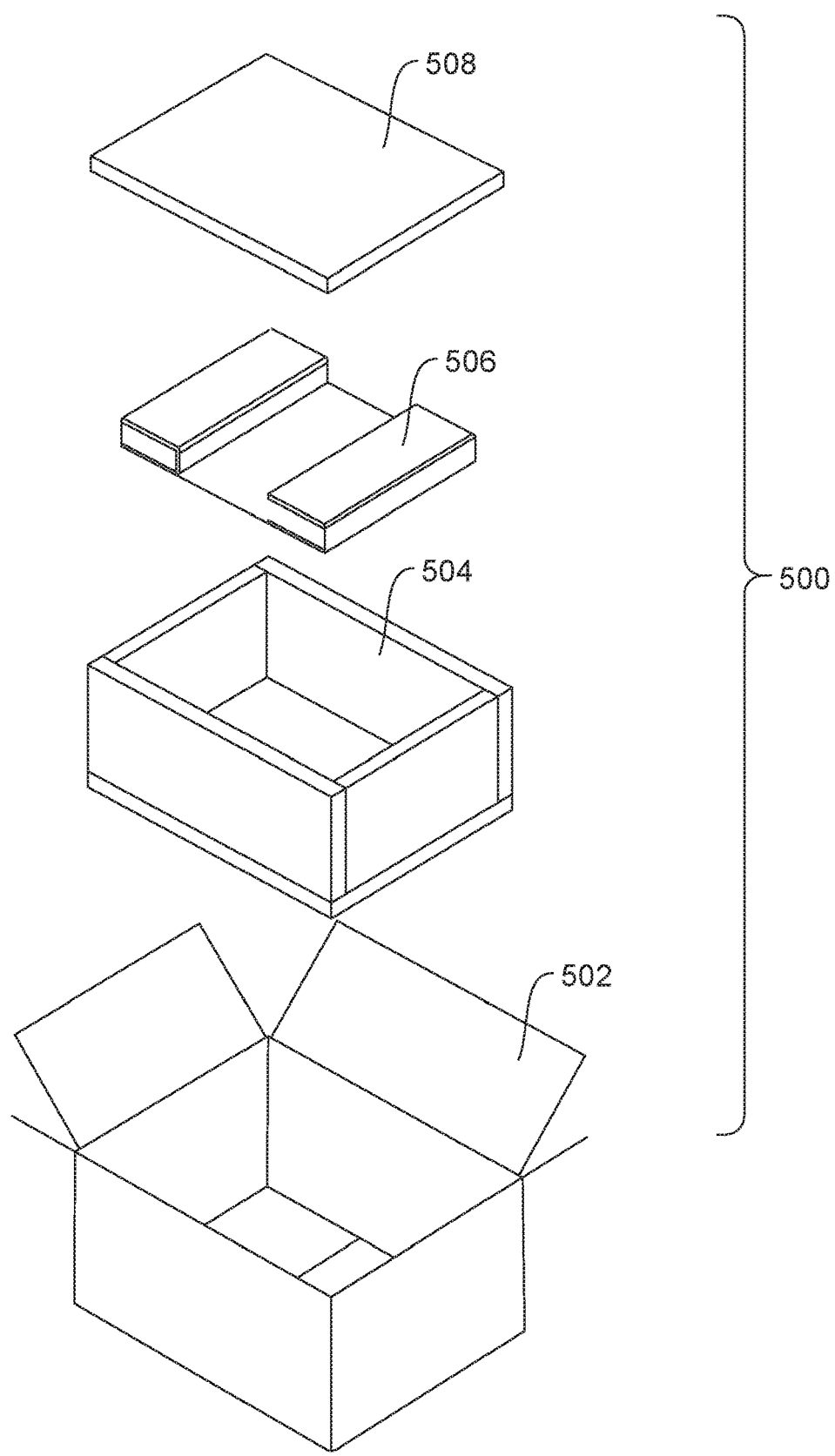
FIG. 5 is an exploded view of a transport container, for holding one or more BPSs, according to some embodiments of the disclosure.

The BPS, in some embodiments, includes a tertiary container/package 300 configured to contain at least one of the secondary package 200 (which itself can contain one or more first packages 100), and can also interlock therewith (see interlocking explanation above). The tertiary package 300 includes (according to some embodiments), a tray 302 and a lid 304, the third tray 302 and third lid 304 that can be configured for removable attachment to one another so as to form the tertiary container/package. The tertiary package 300 can also include at least one barrier film 306 removably sealed to at least one of an exterior side of the tray 302 and lid 304. In some embodiments, at least a portion of the third container is substantially transparent so as to view at least a portion of the first package contained within the second container. As shown in FIG. 4B, a plurality of tertiary packages can be stack (according to some embodiments).

Materials for at least one of the tray/lid combinations for any of the first package, second package and third package, can be plastic material known in the art for use with biological materials. For example, a polyethylene terephthalate (e.g., PETG), and BPA-free copolyester. Preferably, for biocompatibility, such materials meet ISO 10993 and USP Class VI standards, and are manufactured without halogens or ortho-phthalate plasticizers. In some embodiments, a high temperature silicone seal can be used to mate with a tray and provide an air-tight seal. Such materials may be coated (in some embodiments at least partially) by a silicone biocompatible material.

Barrier films can be a sterilized, flexible film that completes an aseptic barrier properties of at least one of the secondary and tertiary packages. For example, clear PVC with a pressure sensitive adhesive (PSA) printed to match a deck surface of the PETG (for example) tray and lid components. Additionally, the film can be printed with instructions for opening (e.g., with a scalpel). The use of a scalpel can assist in preventing sudden, sharp movements that could occur if the film was peeled open.

Some embodiments of the BPS include a transport container 500, as earlier noted, and can comprise a box 502 (plastic, cardboard, and the like), a shock absorbing insert element 504 (e.g., EPS foam tray), an adaptor element 506, a shock absorbing lid 508 (e.g., EPS foam lid), and an environmental sensor (not shown). At least some of such materials enable the product/other components to be protected from light and modulate temperature variation (e.g., foam material). The box 502 is preferably configured to preferably include or otherwise contain the insert element 504, the adaptor 506, and the lid 508. To this end, at least one of the adaptor and the insert element can be configured to hold the 300 tertiary container substantially in place relative to the box 502. The components may include shock and/or insulation properties. The environmental sensor can be configured for monitoring at least one environmental parameter of the interior of the box, such parameters being selected from the group consisting of: shock, temperature, pressure, visible light, and humidity. In addition, the environmental sensor can be configured to monitor movement and forces imparted on the BPS so as to determine if the BPS was mishandled during transit. The sensor may also include GPS and tracking functionality so that it can be easily located in transit. The sensor can be a calibrated MicroDAQ MSR175 data logger to actively monitor and record 3-axis acceleration (for example), as well as air pressure, light, humidity and temperature.

The BPS, or components thereof, according to some embodiments, may include the following additional features, and/or clarifications:
  a barrier(s) to limit $CO_2$ and $O_2$ gas exchange;
  appropriate labeling;
  ease of opening in a surgical environment;
  reusable; and
  maintain environmental conditions (e.g., temperature, pressure, humidity).

Accordingly, the BPS according to at least some of the above-noted embodiments includes a packaging methodology for packaging a biological tissue. Such methodology can include one or more, and in some embodiments, a plurality of, and in some embodiments, all of the following steps. First, a packaging area for packaging a biological tissue in the BPS, is provided, e.g., a laminar flow hood (e.g., Biological Safety Cabinet, or BSC) is provided, which is cleaned/sterilized (e.g., as per procedure SOP-000010, "*Operation and Cleaning of Baker Biosafety Cabinet*," herein incorporated by reference). This process, according to some embodiments, may be performed in an ISO 14644-1 Class 7 (Federal Standard 209 Class 10,000) clean room with an ISO 14644-1 Class 5 (FS 209 Class 100) biological safety cabinet (BSC). A liquid transport medium for the biological tissue is warmed to approximately 37° C. via, e.g., a water bath. A plurality of prefilled syringes, which include a predetermined amount of transport media (e.g., 50 mL, 50 mL and 45 mL, respectively).

Each component of the BPS according to some embodiments is provided, as well as other components which may be used to load tissue and/or media into the packaging (e.g., syringes noted above):

the first package (a pouch with an open end and clamshell package), the second package, and tertiary package (each having been sterilized);
one or more, and preferably, a plurality of tubes for use with the pouch;
heat-sealing equipment to seal the tubes by creating, e.g., two (2) seals a predetermined distance: apart, and from an edge of the pouch;
wipes for wiping the bag; and
luer lock(s), luer or needleless access, and associated pin(s) into respective ports of the pouch.

Next, a biological tissue is placed on the base/raised platform of the tray of the clamshell, and a predetermined amount of transport media is added so as to keep the tissue moist. The lid of the clamshell is then secured to the tray (and thus forming the clamshell). The clamshell containing the tissue is then placed into the open pouch, the open end thereof sealed (via, e.g., heat sealing, and/or adhesive). Via one and/or another of the ports in the pouch, the pouch is filled with transport media (the ports optionally include respective luer locks), with one of the ports performing as liquid transport, and the other as air escape means. This process is preferably accomplished with the use of syringes for at least one of filling with media and removing the air (one component of which can be one and/or another of the syringes noted above).

Thereafter, the pouch with the clamshell therein (i.e., the first package) is placed within the secondary package (or a plurality of the first packages), sealed (e.g., via at least one of the barrier film, and lid), then the secondary package (or a plurality thereof), is placed within the tertiary package and sealed (again, via at least one of the barrier film and lid). The tertiary package may then be placed in a transport/shipping box for delivery to a healthcare/medical facility for use on a patient(s).

While various inventive embodiments have been described and illustrated herein, those of ordinary skill in the art will readily envision a variety of other means, functionality, steps, and/or structures for performing the functions, obtaining the results, and/or one or more of the advantages described herein, and each of such variations and/or modifications is deemed to be within the scope of the inventive embodiments of this disclosure. More generally, those skilled in the art will readily appreciate that all structures, parameters, dimensions, materials, functionality, steps, and configurations described herein, are meant to be an example and that the actual structure, parameters, dimensions, materials, functionality, steps, and configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the claims supported by the present disclosure, and equivalents thereto, inventive embodiments may be practiced otherwise than as specifically described and claimed. Inventive embodiments of the present disclosure are also directed to each individual feature, system, article, structure, material, kit, functionality, step, and method described herein. In addition, any combination of two or more such features, systems, articles, structure, materials, kits, functionalities, steps, and methods, if such are not mutually inconsistent, is included within the inventive scope of the present disclosure. Some embodiments may be distinguishable from the prior art for specifically lacking one or more features/elements/functionality (i.e., claims directed to such embodiments can include negative limitations).

Also, as noted, various inventive concepts are embodied as one or more methods, of which examples have been provided herein. The acts performed as part of the methods may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. A biological tissue packaging and transport system comprising a first package, a secondary package, a tertiary package, and a transport container, wherein:
   each of the first, secondary, and tertiary package is sanitized or sterilized prior to packaging of a biological tissue therein;
   the first package comprises a pouch, a first tray, and a first lid, the first tray and first lid configured for removable snap-fit attachment to one another so as to form a clamshell container;
   the first tray includes:
      at least one tray channel and at least one tray projecting portion arranged along the perimeter of the first tray, and
      a raised portion, relative to the at least one tray channel, arranged within the perimeter of the first tray and configured:
         for arrangement of the biological tissue thereon,
         to accept placement of the biological tissue and a clipped or sutured perimeter of the biological tissue to extend over or into the at least one tray channel; and
         to include a knurled surface, a recessed area arranged substantially in the center of the raised portion so as to provide relief for an identifying suture;
   the first lid includes:
      a finger-lift tab, a plurality of protrusions configured to hold clips along the perimeter, and at least one lid channel and at least one lid projecting portion arranged along a perimeter of the first lid and configured to mate with at least one of the tray channel and the tray projecting portion, wherein the lid projecting portion includes a surface configured to at least one of contact and hold a perimeter of the biological tissue arranged on the raised portion of the first tray,
      a pair of holes, each located in a respective, opposed corner of the first lid and configured to expedite the removal of trapped air within the clamshell container during a liquid transport media filing process; and
      a plurality of dimples configured to project out from an inner surface of the first lid and configured to at least one of:
         establish a tortuous path for the transport media upon flowing over the biological tissue,
         reduce the velocity of the flow of the transport media,
         limit contact area of the first lid on the biological tissue, and
         limit potential damage to the biological tissue due to movement of the biological tissue towards and contact with the first lid;
   the pouch includes:
      a sealable portion configured to receive the clamshell container,
      at least one sealable port configured to receive the liquid transport media or to evacuate air from at least an interior of the pouch, and
      at least one substantially transparent portion for viewing at least a portion of the clamshell container arranged within the pouch,
   the clamshell container is configured to:
      house the biological tissue and the liquid transport media, and
      minimize movement of the transport media;
   the secondary package is configured to contain the first package and interlock therewith, and comprises:
      a second tray and a second lid, the second tray and second lid configured for removable attachment to one another so as to form a second container;
      wherein:
         at least a portion of the second container is substantially transparent so as to view at least a portion of the first package contained therein, and
         the second container is configured to be substantially gas impermeable;
   the tertiary package is configured to contain the secondary package and interlock therewith, and comprises:
      a third tray and a third lid, the third tray and third lid configured for removable attachment to one another so as to form a tertiary container, and
      at least one barrier film removably sealed to at least one of an exterior side of the third tray and third lid;
      wherein at least a portion of the third container is substantially transparent so as to view at least a portion of the first package contained within the second container;
   the transport container comprises a box, a shock absorbing insert element, an adaptor element, a shock absorbing lid, and an environmental sensor, wherein:
      the box is configured to contain the insert element, the adaptor element, and the shock absorbing lid,
      at least one of the adaptor element and the insert element is configured to hold the tertiary container substantially in place relative to the box, and
      the environmental sensor is configured for monitoring at least one environmental parameter of the interior of the box.

2. A biological tissue packaging and transport system comprising a first package, a secondary package, a tertiary package, and a transport container, wherein:

each of the first, secondary, and tertiary package is sterilized prior to packaging of a biological tissue therein;
the first package comprises a pouch, and a first tray and a first lid configured for removable snap-fit attachment to one another so as to form a clamshell container;
the clamshell container is configured to:
  house the biological tissue and liquid transport media, and
  minimize movement of the transport media,
the first tray includes:
  at least one tray channel and at least one tray projecting portion arranged along the perimeter of the first tray, and
  a raised portion, relative to the at least one tray channel, arranged within the perimeter of the first tray and configured:
    for arrangement of the biological tissue thereon,
    to accept placement of the biological tissue and a clipped or sutured perimeter of the biological tissue to extend over or into the at least one tray channel;
    and
    to include a knurled surface, a recessed area arranged substantially in the center of the raised portion so as to provide relief for an identifying suture;
the first lid includes:
  a finger-lift tab, a plurality of protrusions configured to hold clips along the perimeter, and at least one lid channel and at least one lid projecting portion arranged along a perimeter of the first lid and configured to mate with at least one of the tray channel and the tray projecting portion, wherein the lid projecting portion includes a surface configured to at least one of contact and hold a perimeter of the biological tissue arranged on the raised portion of the first tray,
  a pair of holes, each located in a respective, opposed corner of the first lid and configured to expedite the removal of trapped air within the clamshell container during a liquid media filing process;
  and
  a plurality of dimples configured to project out from an inner surface of the first lid and configured to at least one of:
    establish a tortuous path for the transport media upon flowing over the biological tissue,
    reduce the velocity of the flow of the transport media,
    limit contact area of the first lid on the biological tissue, and
    limit potential damage to the biological tissue due to movement of the biological tissue towards and contact with the first lid;
the pouch includes:
  a sealable portion configured to receive the clamshell container, at least one first sealable port configured to receive the liquid transport media, and at least one second sealable port configured to evacuate air from at least an interior of the pouch,
  and
  at least one substantially transparent portion for viewing at least a portion of the clamshell container arranged within the pouch;
the secondary package is configured to contain the first package and interlock therewith, and comprises:
  a second tray and a second lid, the second tray and second lid configured for removable attachment to one another so as to form a second container,
  and
  at least one secondary barrier film removably sealed to at least one of an exterior side of the second tray and second lid;
  wherein:
    at least a portion of the second container is substantially transparent so as to view at least a portion of the first package contained therein,
    and
    the second container is configured to be substantially gas impermeable;
the tertiary package is configured to contain the secondary package and interlock therewith, and comprises:
  a third tray and a third lid, the third tray and third lid configured for removable attachment to one another so as to form a tertiary container,
  and
  at least one tertiary barrier film removably sealed to at least one of an exterior side of the third tray and third lid;
  wherein at least a portion of the third container is substantially transparent so as to view at least a portion of the first package contained within the second container;
the transport container comprises a box, a shock absorbing insert element, an adaptor element, a shock absorbing lid, and an environmental sensor, wherein:
  the box is configured to contain the insert element, the adaptor element, and the shock absorbing lid,
  at least one of the adaptor element and the insert element is configured to hold the tertiary container substantially in place relative to the box,
  and
  the environmental sensor is configured for monitoring at least one environmental parameter of the interior of the box.

3. A biological tissue packaging and transport system comprising a first package, a secondary package, a tertiary package, and a transport container, wherein:
  each of the first, secondary, and tertiary package is sanitized or sterilized prior to packaging of a biological tissue therein;
  the first package comprises a pouch, a first tray, and a first lid, the first tray and first lid configured for removable snap-fit attachment to one another so as to form a clamshell container;
  the clamshell container is configured to:
    house the biological tissue and liquid transport media, and
    minimize movement of the transport media,
  the first tray includes:
    at least one tray channel and at least one tray projecting portion arranged along the perimeter of the first tray, and
    a raised portion, relative to the at least one tray channel, arranged within the perimeter of the first tray and configured:
      for arrangement of the biological tissue thereon,
      to accept placement of the biological tissue and a clipped or sutured perimeter of the biological tissue to extend over or into the at least one tray channel;

and
to include a knurled surface, a recessed area arranged substantially in the center of the raised portion so as to provide relief for an identifying suture;

the first lid includes:
a finger-lift tab, a plurality of protrusions configured to hold clips along the perimeter, and at least one lid channel and at least one lid projecting portion arranged along a perimeter of the first lid and configured to mate with at least one of the tray channel and the tray projecting portion, wherein the lid projecting portion includes a surface configured to at least one of contact and hold a perimeter of the biological tissue arranged on the raised portion of the first tray, a pair of holes, each located in a respective, opposed corner of the first lid and configured to expedite the removal of trapped air within the clamshell container during a filing process of the liquid transport media; and a plurality of dimples configured to project out from an inner surface of the first lid and configured to at least one of:
establish a tortuous path for the transport media upon flowing over the biological tissue,
reduce the velocity of the flow of the transport media,
limit contact area of the first lid on the biological tissue, and
limit potential damage to the biological tissue due to movement of the biological tissue towards and contact with the first lid;

the pouch includes:
a sealable portion configured to receive the clamshell container,
at least one sealable port configured to at least receive the liquid transport media, and
at least one substantially transparent portion for viewing at least a portion of the clamshell container arranged within the pouch, the secondary package is configured to contain the first package and interlock therewith, and comprises:
a second tray and a second lid, the second tray and second lid configured for removable attachment to one another so as to form a second container;
wherein:
at least a portion of the second container is substantially transparent so as to view at least a portion of the first package contained therein,
and
the second container is configured to be substantially gas impermeable;

the tertiary package is configured to contain the secondary package and interlock therewith, and comprises:
a third tray and a third lid, the third tray and third lid configured for removable attachment to one another so as to form a tertiary container,
and
at least one barrier film removably sealed to at least one of an exterior side of the third tray and third lid;
wherein at least a portion of the third container is substantially transparent so as to view at least a portion of the first package contained within the second container;

the transport container comprises a box, a shock absorbing insert element, an adaptor element, a shock absorbing lid, and an environmental sensor, wherein:
the box is configured to contain the insert element, the adaptor element, and the shock absorbing lid,
at least one of the adaptor element and the insert element is configured to hold the tertiary container substantially in place relative to the box,
and
the environmental sensor is configured for monitoring at least one environmental parameter of the interior of the box.

* * * * *